(12) United States Patent
Viola

(10) Patent No.: US 7,753,248 B2
(45) Date of Patent: Jul. 13, 2010

(54) SURGICAL INSTRUMENT WITH FLEXIBLE DRIVE MECHANISM

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/478,415

(22) Filed: Jun. 4, 2009

(65) Prior Publication Data

US 2009/0236393 A1    Sep. 24, 2009

Related U.S. Application Data

(63) Continuation of application No. 11/893,312, filed on Aug. 15, 2007, now Pat. No. 7,556,185.

(51) Int. Cl.
*A61B 17/068* (2006.01)

(52) U.S. Cl. .................. 227/175.1; 227/19; 606/139; 606/219; 173/178; 173/205

(58) Field of Classification Search ............. 227/175.1, 227/19, 178.1, 176.1, 180.1; 173/178, 205; 606/139, 219, 153
See application file for complete search history.

(56) References Cited

U.S. PATENT DOCUMENTS

| | | |
|---|---|---|
| 4,331,277 A | 5/1982 | Green |
| 4,606,343 A | 8/1986 | Conta et al. |
| 4,644,950 A | 2/1987 | Valli |
| 4,936,845 A | 6/1990 | Stevens |
| 5,237,884 A | 8/1993 | Seto |
| 5,249,583 A | 10/1993 | Mallaby |
| 5,312,023 A | 5/1994 | Green et al. |
| 5,326,013 A | 7/1994 | Green et al. |
| 5,350,355 A | 9/1994 | Sklar |
| 5,381,943 A | 1/1995 | Allen et al. |
| 5,389,098 A | 2/1995 | Tsuruta et al. |
| 5,467,911 A | 11/1995 | Tsuruta et al. |
| 5,518,163 A | 5/1996 | Hooven |
| 5,518,164 A | 5/1996 | Hooven |
| 5,591,170 A | 1/1997 | Spievack et al. |
| 5,628,446 A | 5/1997 | Geiste et al. |
| 5,653,374 A | 8/1997 | Young et al. |
| 5,667,517 A | 9/1997 | Hooven |

(Continued)

FOREIGN PATENT DOCUMENTS

WO    WO 97/29694 A    8/1997

(Continued)

OTHER PUBLICATIONS

European Search Report for EP 08252692.2-2310 date of completion is Nov. 27, 2008 (9 pages).

*Primary Examiner*—Scott A. Smith

(57) ABSTRACT

A drive mechanism for use with a surgical instrument includes a rotatable drive member, a crank operatively coupled to the drive member; a clutch operatively coupled to the crank, wherein rotational motion of the drive member causes oscillating movement of the clutch; and a gear rotatably coupled to the clutch, wherein the oscillating movement of the clutch causes rotation of the gear. The drive mechanism may further include a gear configured to engage a linear member. The crank may include a pin extending distally therefrom. The clutch may include a slot dimensioned and configured to receive a pin of the crank.

14 Claims, 12 Drawing Sheets

U.S. PATENT DOCUMENTS

| | | | |
|---|---|---|---|
| 5,779,130 | A | 7/1998 | Alesi et al. |
| 5,782,397 | A | 7/1998 | Koukline |
| 5,954,259 | A | 9/1999 | Viola et al. |
| 6,119,913 | A | 9/2000 | Adams et al. |
| 6,461,372 | B1 | 10/2002 | Jensen et al. |
| 6,533,157 | B1 | 3/2003 | Whitman |
| 6,699,177 | B1 | 3/2004 | Wang et al. |
| 6,716,233 | B1 | 4/2004 | Whitman |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,953,139 | B2 | 10/2005 | Milliman et al. |
| 6,981,941 | B2 | 1/2006 | Whitman et al. |
| 7,111,769 | B2 | 9/2006 | Wales et al. |
| 7,128,253 | B2 | 10/2006 | Mastri et al. |
| 7,422,136 | B1 | 9/2008 | Marczyk |
| 7,461,767 | B2 | 12/2008 | Viola et al. |
| 7,464,846 | B2 | 12/2008 | Shelton et al. |
| 7,556,185 | B2 * | 7/2009 | Viola ..................... 227/175.1 |
| 2006/0151567 | A1 | 7/2006 | Roy |

FOREIGN PATENT DOCUMENTS

| | | |
|---|---|---|
| WO | WO 2007/030753 A | 3/2007 |
| WO | WO 2007/118179 A | 10/2007 |

* cited by examiner

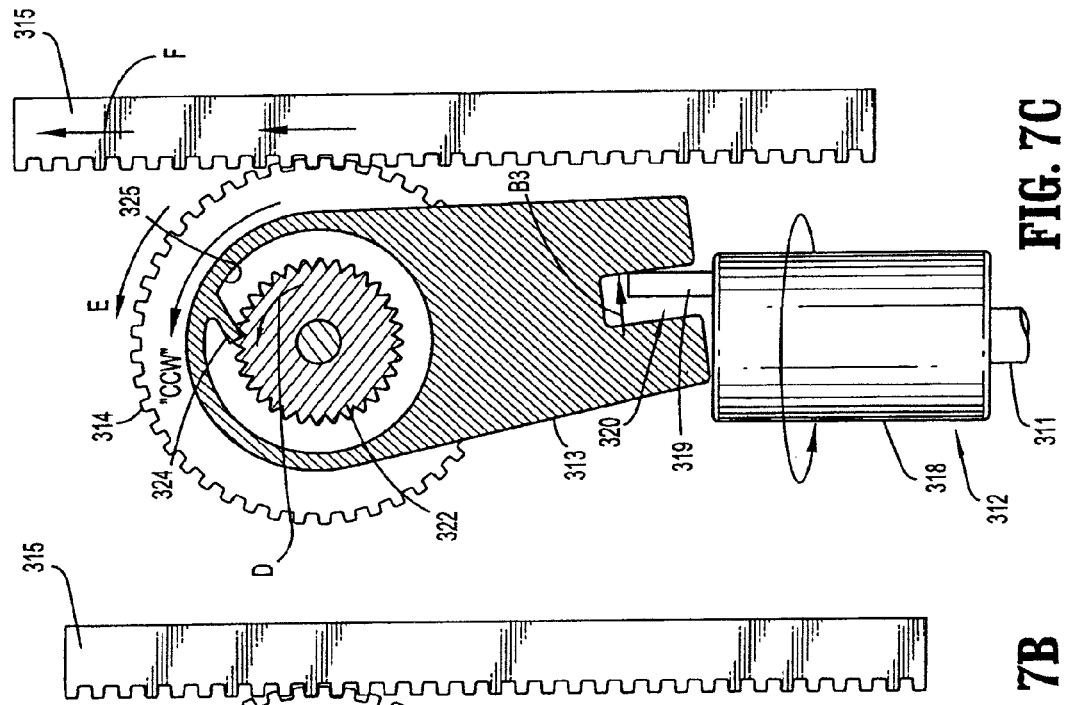
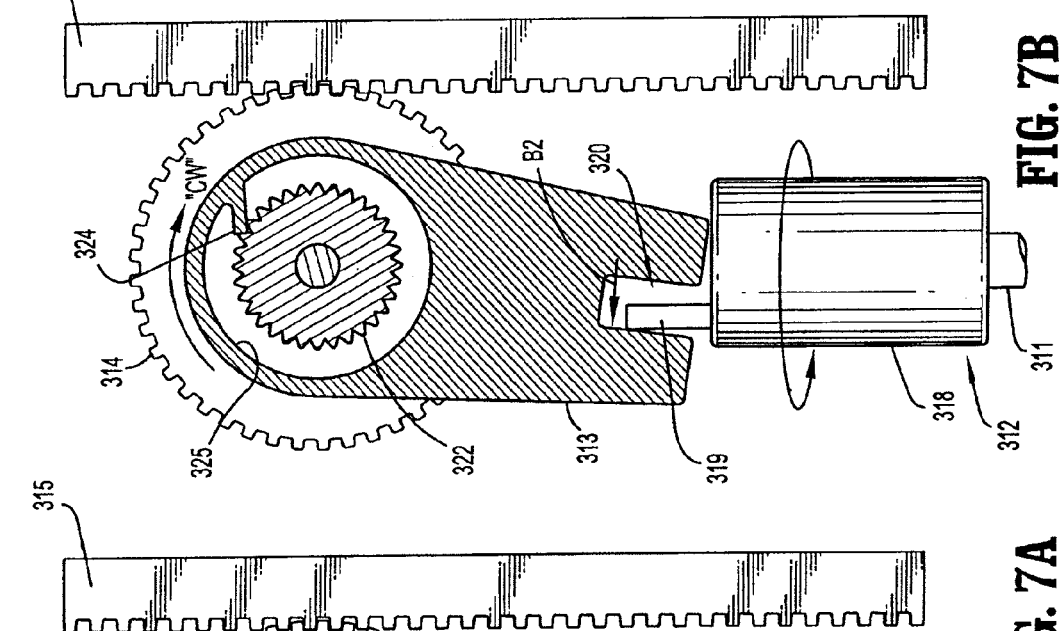
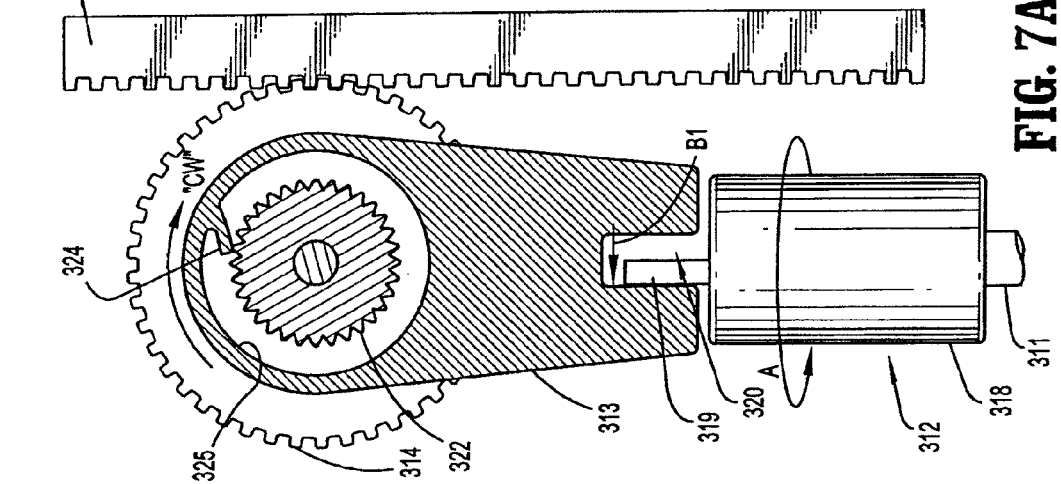

SURGICAL INSTRUMENT WITH FLEXIBLE DRIVE MECHANISM

CROSS-REFERENCE TO RELATED APPLICATIONS

This application is a continuation of U.S. application Ser. No. 11/893,312 filed Aug. 15, 2007, now U.S. Pat. No. 7,556,185 and the disclosures of each of the above-identified applications are hereby incorporated by reference in their entirety.

BACKGROUND

1. Technical Field

The present invention relates to surgical instruments and more particularly, to an endoscopic surgical instrument having a flexible drive mechanism.

2. Background of Related Art

Articulating surgical instruments are well-known in the art. Surgeons typically use articulating instruments to reach areas out of line with the entry axis of the surgical instrument. Ordinarily, articulating surgical instruments transmit energy along a longitudinal axis of the instrument, and do not effectively transmit large amounts of energy when the end effector is articulated at sharp angles. Surgical instruments that use high force/low velocity methods often require physically large components. These physically large components are usually quite rigid and are not easily bent.

The operation of current articulating surgical instruments involves the movement of a rod or a long flexible metal strip actuator around a bend. The use of such structural elements leads to, among other things, friction and buckling. These adverse consequences are normally minimized by restricting the maximum bend angle of surgical instruments to approximately 45 degrees.

For instance, U.S. Pat. No. 5,381,943 to Allen et al. discloses an endoscopic surgical stapling instrument comprising a pivotable staple head assembly mounted on the distal end of a support tube. The instrument includes a handle assembly and a saddle-shaped actuator slidably mounted thereon for controlling the pivotal movement of the staple head assembly. An articulation driver is mounted inside the support tube. The articulation driver is formed by an elongated thin flat rod. In operation, the saddle-shaped actuator moves a slide member coupled to a driver coupling member to operate the articulation driver. The articulation driver pivots the stapling head assembly in response to movement of the saddle-shaped actuator. The staple head assembly can be articulated to angles of 15, 30, 45 and 60 degrees relative to the support tube.

In light of current articulating surgical instruments shortcomings, it would be beneficial to provide a surgical instrument capable of bending at angles of at least 90 degrees and transmit the energy required to operate a surgical tool, such as an end effector. It would also be desirable to provide a surgical instrument capable of transmitting large amounts of force at very large angles using simple and reliable structural elements. Therefore, a need exists for a reliable surgical stapling device and a mechanism for use therewith that will allow a user to operate a surgical tool at angles of at least 90 degrees relative to the entry axis of the surgical instrument.

SUMMARY OF THE INVENTION

The present application discloses a surgical instrument and a mechanism for use therewith capable of articulating at least 90 degrees with respect to a longitudinal axis defined therealong, and applying the force necessary to operate a surgical tool disposed at a distal end thereof. The mechanism includes a drive member having proximal and distal ends, a crank mechanism operatively connected to the distal end of the drive member, a clutch coupled to the crank mechanism, and a gear rotatable about a central axis and configured to engage a linear driver. The drive member is rotatable and may be flexible. A handle portion attached to the proximal end of the drive member may provide the necessary motion to rotate the drive member. Many types of handle assemblies may be employed to provide rotational motion to the drive member. The rotational motion of the drive member rotates a crank mechanism.

The crank mechanism converts the low torque rotational motion of the drive member into a high torque rocking motion of just a few degrees. The crank mechanism may include a rod member and a pin extending distally thereof. The pin itself undergoes a circulating and rocking motion as the drive member rotates. The pin is configured to interact with a slot of the clutch.

The clutch transforms the rocking motion of the crank mechanism into rotational motion, thereby rotating a gear connected thereto. The gear may be substituted for a sprocket or a similar driver known in the art. The rotational motion of the gear causes the linear driver to translate.

The linear driver is operatively connected to the gear. The linear driver may be comprised of a rack, a chain or a similar driver. As the gear rotates, the linear driver translates to operate a surgical tool. The instrument hereinabove described has a high mechanical advantage.

These and other features of the mechanism of the subject application will become more readily apparent to those skilled in the art from the following detailed description of the embodiments of the device taken in conjunction with the drawings.

BRIEF DESCRIPTION OF THE DRAWINGS

Various embodiments of the surgical instrument and the mechanism for use therewith of the present disclosure will be described hereinbelow with reference to the drawings wherein:

FIG. 5AA is a top cross-sectional view of a portion of the drive mechanism of FIG. 5A, taken along section lines 5AA-5AA of FIG. 5A;

FIG. 5AB is an exploded perspective view of the portion of the drive mechanism of FIG. 5A;

FIG. 5AC is a top cross-sectional view of the drive mechanism of FIG. 5A in a first position;

FIG. 5AD is a top cross-sectional view of the drive mechanism of FIG. 5A during movement of a gear in a first direction;

FIG. 5AE is a top cross-sectional view of the drive mechanism of FIG. 5A during movement of a gear in a second direction;

FIG. 5BA is a top cross-sectional view of the drive mechanism of FIG. 5B in a first position, taken along section lines 5BA-5BA of FIG. 5B;

FIG. 5BB is a top cross-sectional view of the drive mechanism of FIG. 5B during movement of a gear in a first direction;

FIG. 5BC is a top cross-sectional view of the drive mechanism of FIG. 5B during movement of a gear in a second direction;

FIG. 7A is a top cross-sectional view of the drive mechanism of FIGS. 4 and 5 in a first position, taken along section lines 7A-7A of FIG. 4;

FIG. 7B is a top cross-sectional view of the drive mechanism of FIG. 7A during movement of a gear in a first direction; and FIG. 7C is a top cross-sectional view of the mechanism of FIG. 7A during movement of a gear in a second direction.

DETAILED DESCRIPTION

Figure 1:
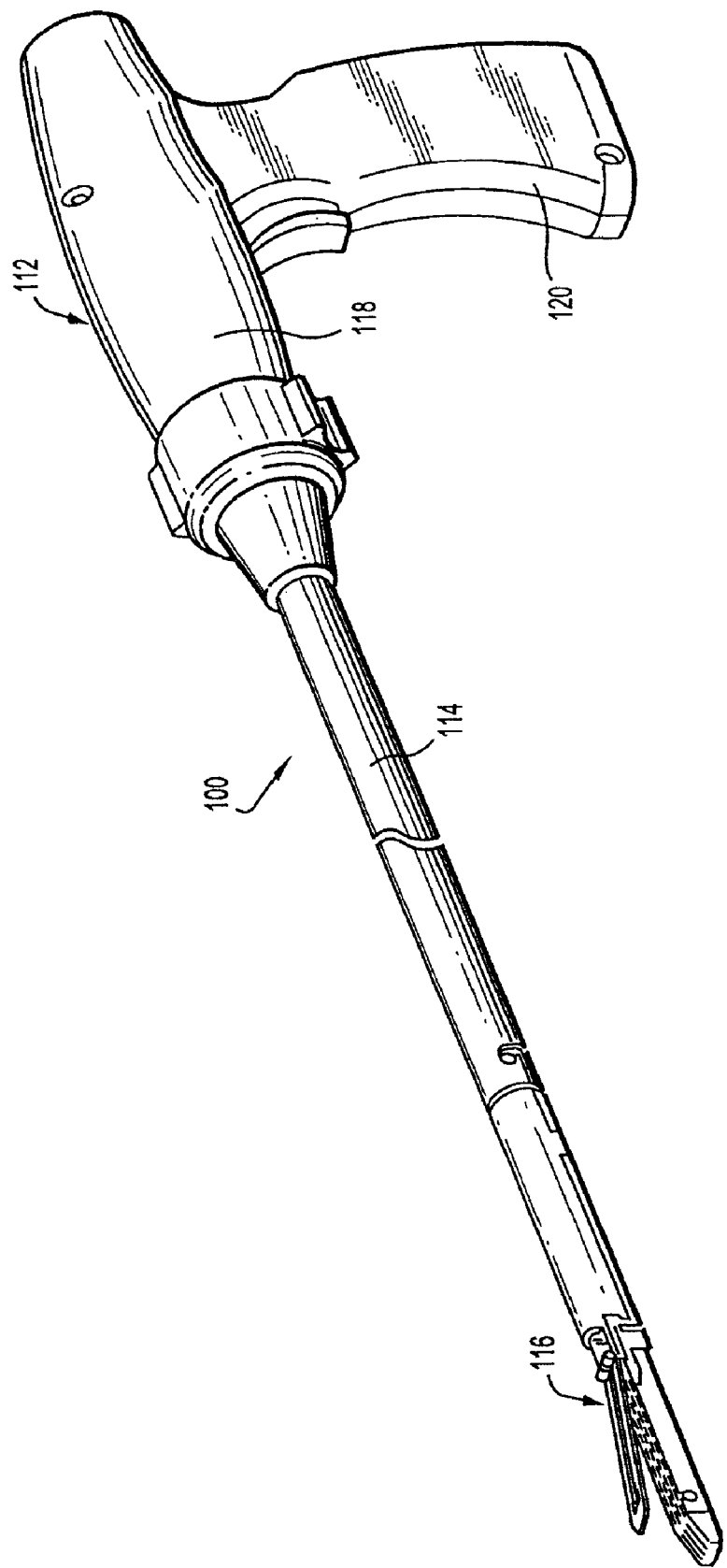
FIG. 1 is a perspective view of a surgical instrument constructed in accordance with an embodiment of the present disclosure.

Embodiments of the presently disclosed surgical instrument and the mechanism for use therewith are now described in detail with reference to the drawings, in which like reference numerals designate identical or corresponding elements in each of the several views. As used herein, the terms "distal" refers to that portion of the surgical instrument, or component thereof, farther from the user while the term "proximal" refers to that portion of the component thereof, closest to the user.

Referring initially to FIG. 1, a surgical instrument in accordance with an embodiment of the present disclosure is referred to in the figures as reference number 100. Briefly, surgical instrument 100 is configured to clamp body tissue and apply a plurality of surgical fasteners to the body tissue during laparoscopic or endoscopic procedures. In particular, surgical instrument 100 is capable of transmitting the force necessary to operate a surgical tool attached to the distal end thereof at angles of at least 90 degrees relative to a longitudinal axis defined by the surgical instrument 100 and includes a drive mechanism described in detail below.

The drive mechanism disclosed in the present disclosure may be used with other types of surgical instruments. Thus, for example, an instrument particularly suited for open surgery can be used. Alternatively, an instrumented suited for laparoscopic or endoscopic surgery may be used. Examples of laparoscopic and endoscopic instruments are disclosed respectively in U.S. Pat. Nos. 5,014,899 and 7,128,253, the entire contents of each is incorporated herein by reference. While the drive mechanism will be primarily discussed in the context of applying staples, it can also be employed in connection with a clip applier, a cutter or any other suitable surgical instrument.

As seen in FIG. 1, surgical instrument 100 includes a handle portion 112, an elongated body portion 114 extending distally from handle portion 112, and a tool assembly 116 connected to a distal end of body portion 114. Elongated body portion 114 may be flexible. Handle portion 112 supplies high velocity, low torque rotation to a shaft through electromechanical means or any other suitable means known in the art. A number of handle assemblies may be employed with surgical instrument 100.

Figure 2:
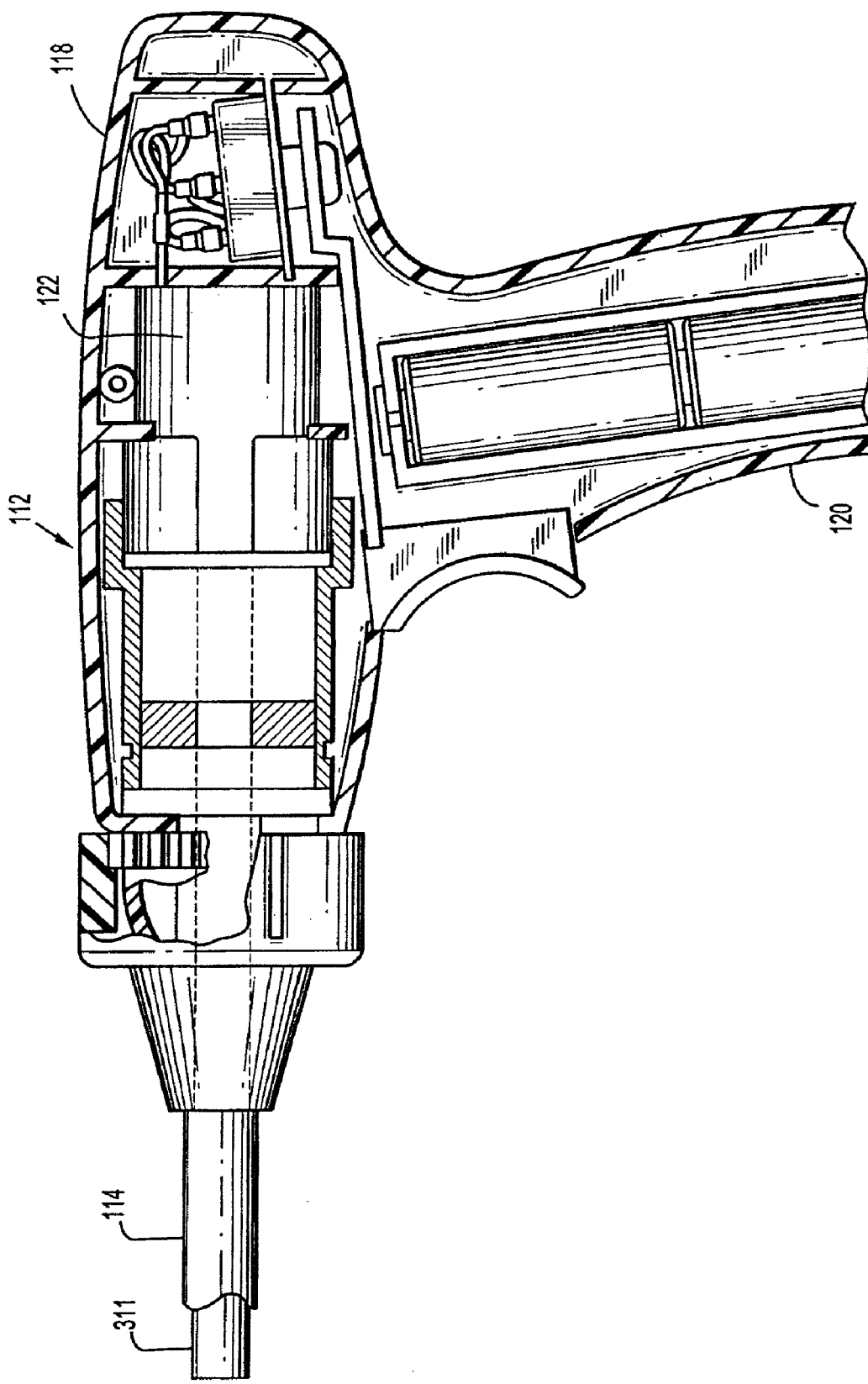
FIG. 2 is an side longitudinal cross-sectional view of a portion of the surgical instrument of FIG. 1.
Figure 2A:
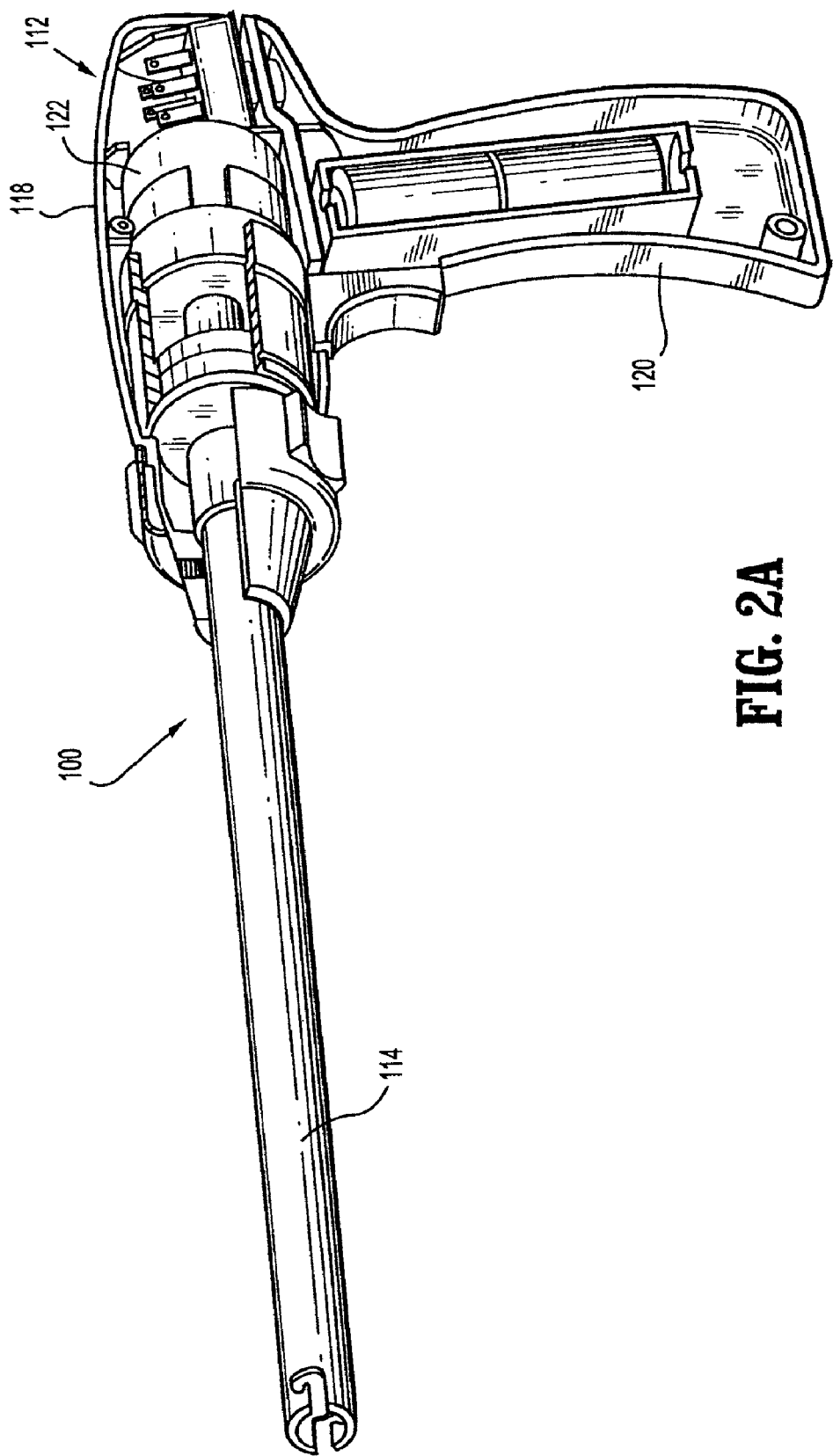
FIG. 2a is a perspective cut away view of a portion of the surgical instrument of FIGS. 1 and 2.

As illustrated in FIGS. 2 and 2a, handle portion 112 includes an elongated barrel section 118 and a handle gripping section 120, as described in U.S. Pat. No. 5,954,259, the entire contents of which is incorporated herein by reference.

A motor assembly 122 is disposed within the barrel section 118 and is operatively coupled to drive member 311. Alternatively, handle portion 112 can include gear box operatively connected to motor assembly 112 to increase or decrease the rotary motion supplied by motor assembly 112. In this embodiment, the gear box is operatively coupled to drive member 311.

Figure 3:
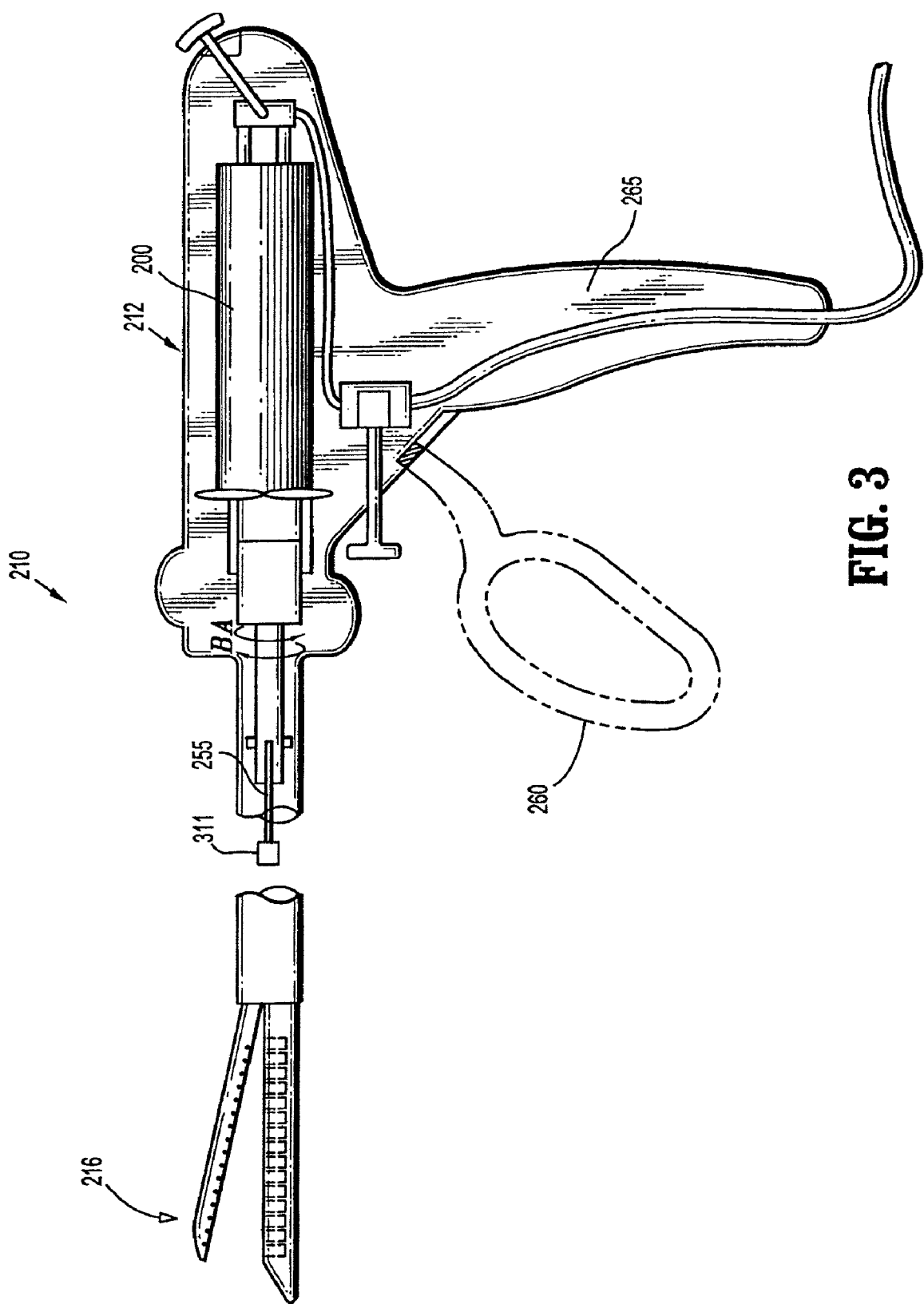
FIG. 3 is side longitudinal cross-sectional view of a portion of a pneumatic powered surgical instrument constructed according to another embodiment of the present disclosure.

Referring to FIG. 3, in an alternative embodiment, handle portion 212 provides rotational motion via pneumatic means, as described in U.S. patent application Ser. No. 10/528,851, the entire contents of which is incorporated herein by reference. In this embodiment, handle portion 212 includes a rotary pneumatic drive assembly 200 housed within handle portion 212 that rotates a shaft 255. Shaft 255 is operatively connected to drive member 311. In addition, handle portion 212 includes a fixed handle 265 formed like a pistol grip to enhance manipulation of the surgical instrument 210 as needed during surgery. Handle portion 212 may also include a movable handle actuator 260 (shown in phantom) that is movable relative to fixed handle 265 for actuating tool assembly 216.

Figure 4:
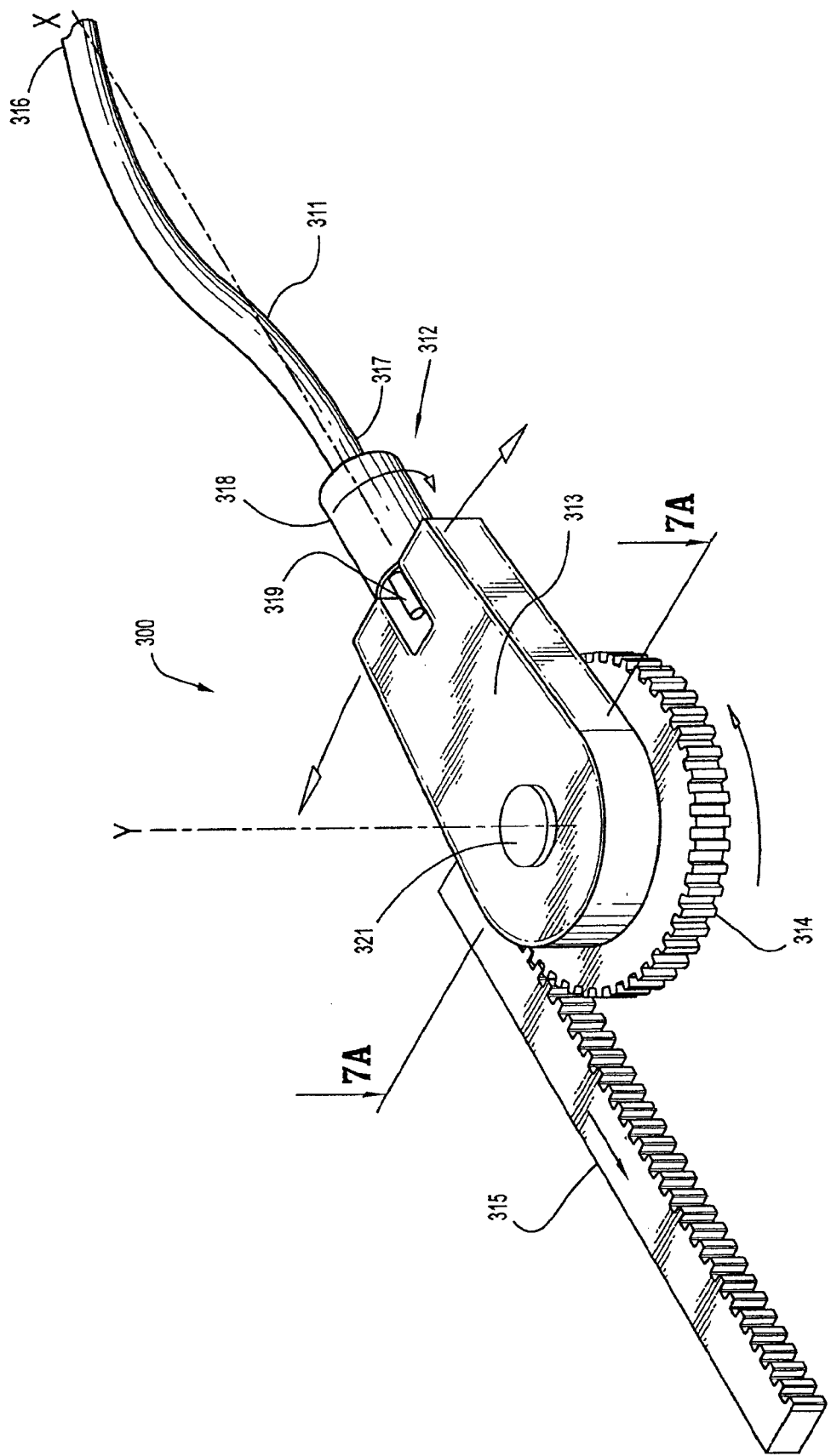
FIG. 4 is a perspective view of a drive mechanism constructed in accordance with an embodiment of the present disclosure.
Figure 5:
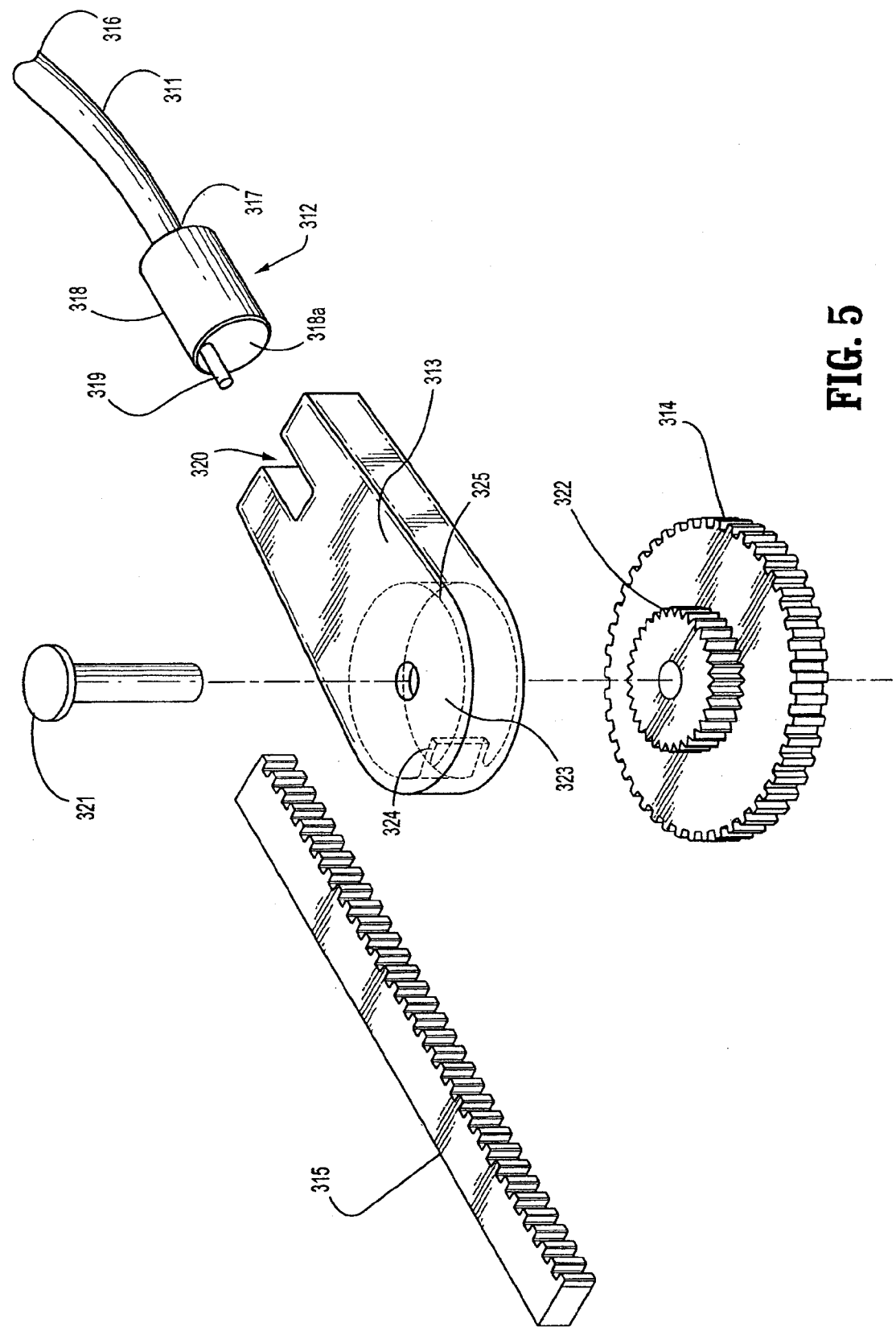
FIG. 5 is an exploded perspective view of the drive mechanism of FIG. 4.

Referring now to FIGS. 4 and 5, mechanism 300 has a drive member 311 operatively connected to a crank mechanism 312, a clutch 313 configured to interact with crank mechanism 312, a fastening device 321 interconnecting crank mechanism 312 and a gear 314, and a linear driver 315 configured to engage gear 314. Drive member 311 may be disposed in mechanical cooperation with either to motor assembly 122 or pneumatic drive assembly 200. One skilled in the art, however, will recognize that other kinds of driving devices may be used with drive mechanism 300. In addition, drive member 311 may be made of a flexible material capable of bending at least 90 degrees with respect to an axis "X".

Drive member 311 has a distal end 317 and a proximal end 316. Proximal end 316 of the drive member 311 is operatively connected to a handle portion 112, 212 or other suitable source of rotational motion. As discussed hereinabove, a number of handle portions may be employed to rotate drive member 311. Distal end 317 of the drive member 311 is operatively connected to a crank mechanism 312. Crank mechanism 312 includes a rod member 318 and a pin 319 extending distally therefrom. Pin 319 extends from a location offset from the center of a distal end surface 318a of rod member 318, and has a cylindrical shape. Other suitable shapes, as recognized by those skilled in the art, may be used for pin 319. Additionally, pin 319 is positioned within a slot 320 of a clutch 313.

Clutch 313 is operatively coupled to crank mechanism 312, and includes a substantially annular space 323 defined therein, a slot 320 dimensioned for receiving pin 319, and a gear 322 positioned in annular space 323. Gear 322 can be a toothed wheel. Annular space 323 is dimensioned and configured to receive gear 322. Inner wall 325 of clutch 313 defines annular space 323. A protrusion 324 extends from inner wall 325 to the periphery of gear 322. A fastening member 321 interconnects clutch 313 and a gear 314.

Figure 5A:
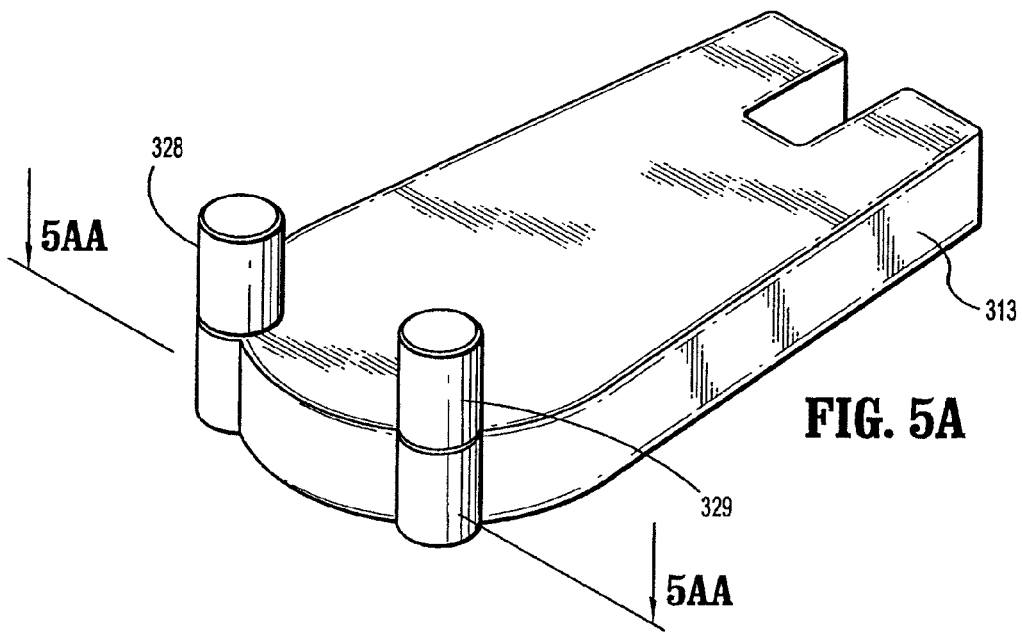
FIG. 5A is a perspective view of a portion of a drive mechanism according to an embodiment of the present disclosure.
Figure 5A:
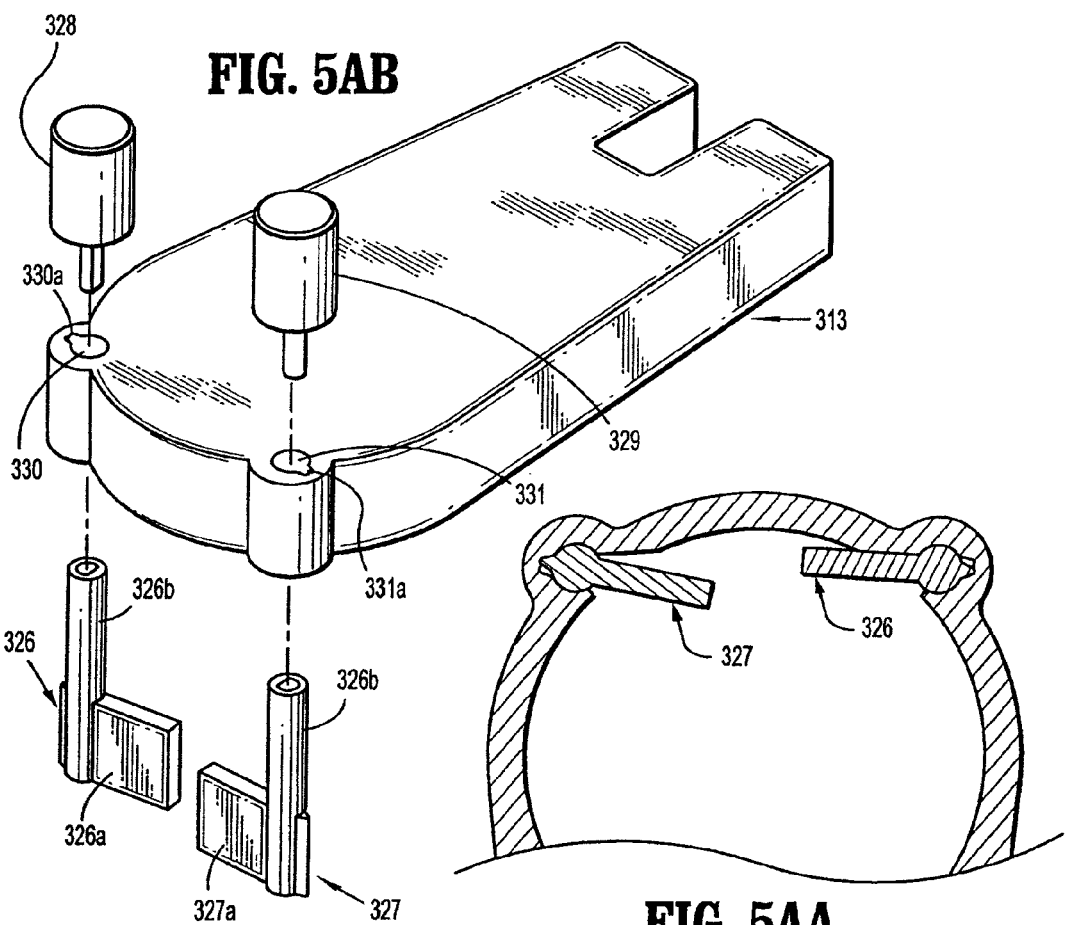
Figure 5A:
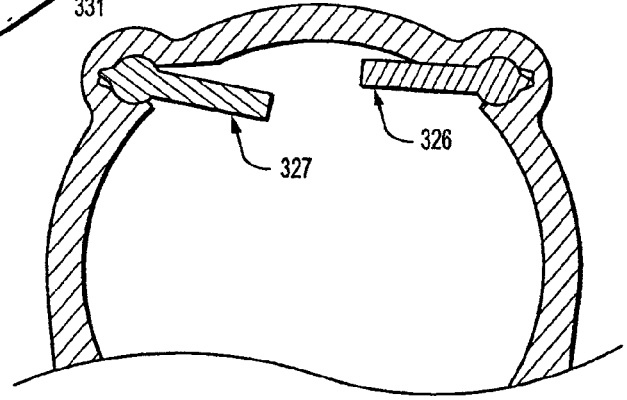
Figure 5A:
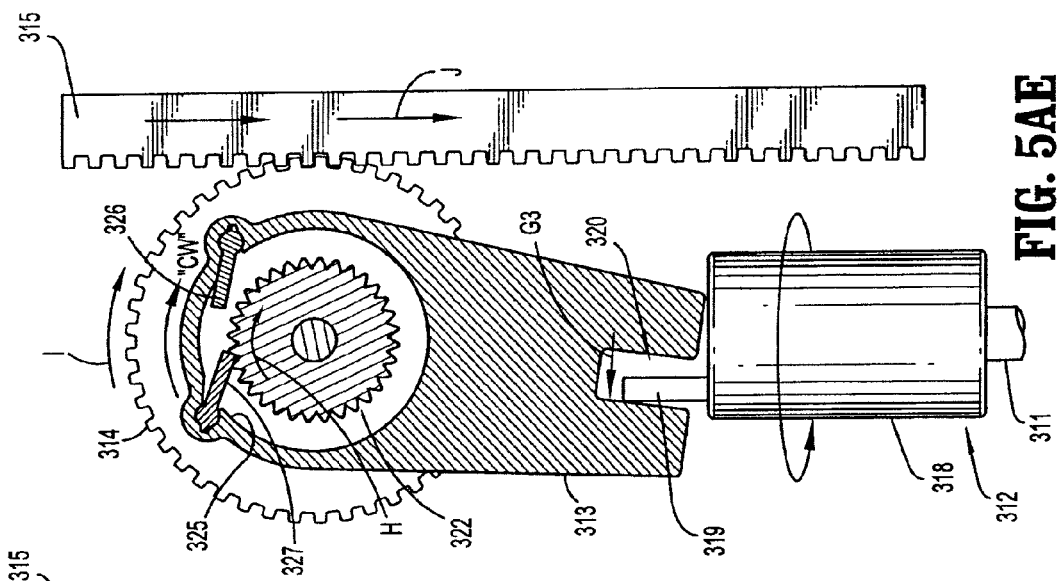
Figure 5A:
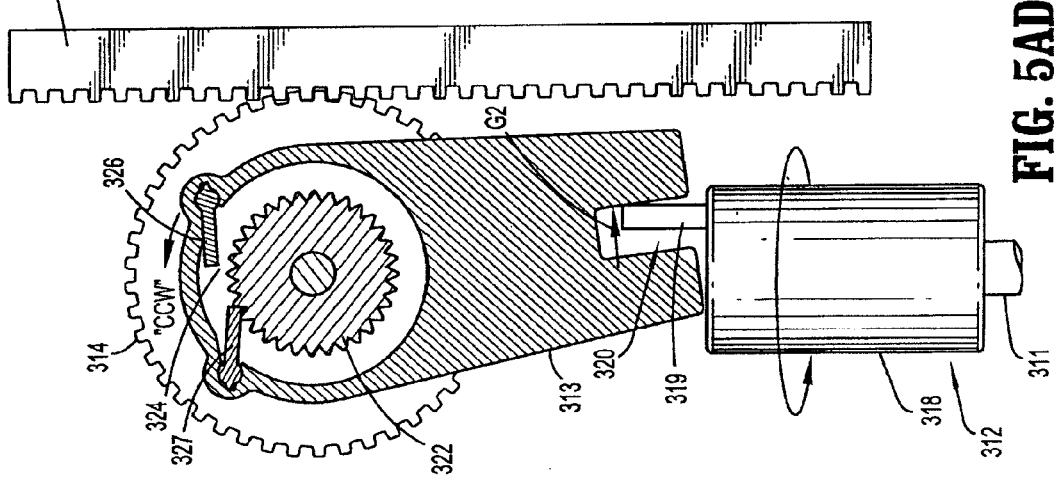
Figure 5A:
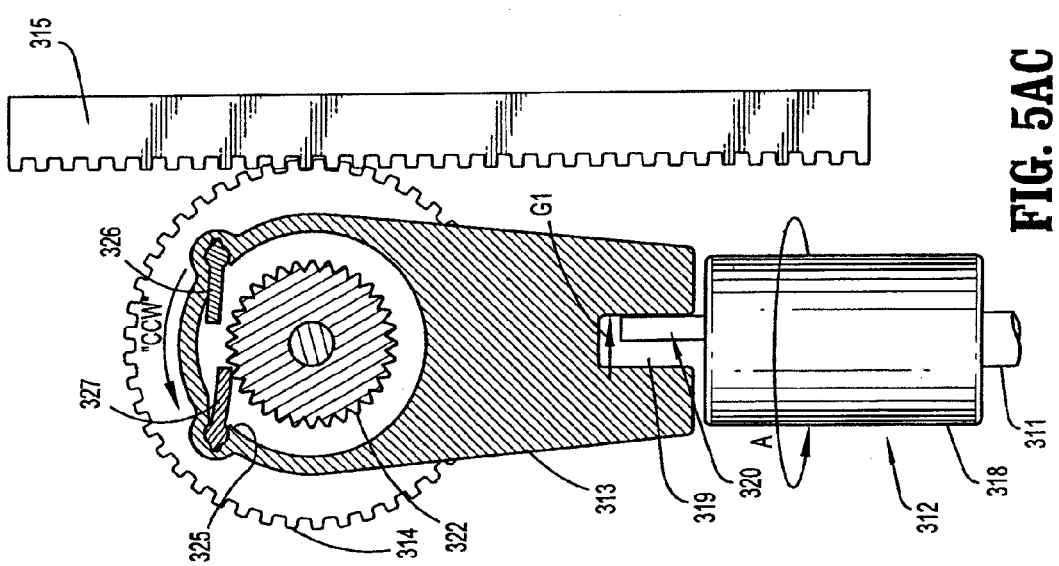

With reference to FIGS. 5A, 5AA, and 5AB, in another embodiment, clutch 313 includes first and second protrusions 326a, 326b facing opposite directions. First and second protrusions 326, 327 are selectively movable to engage gear 322.

In one embodiment, first protrusion 326 has an engagement section 326a and a coupling section 326b. Likewise, second protrusion 327 may include an engagement section 327a and a coupling section 326b. To facilitate movement of protrusions 326a, 326b, protrusions 326a, 326b are operatively coupled to knobs 328, 329, respectively. Specifically, knob 328 is disposed in mechanical cooperation with coupling section 326b of first protrusion 326 whereas knob 329 is disposed in mechanical cooperation with coupling section 326b of second protrusion 326. At least a portion of coupling sections 326b, 327b are disposed in bores 330, 331 of clutch 313. Bores 330, 331 are adapted to receive at least a portion of coupling sections 326b, 327b. Each bore 330, 331 includes a detent 330a, 331a for releasably securing first and second protrusions 326, 327 in place. As will be discussed in detail below, during operation, first protrusion 326 allows distal translation of linear drive 315 while second protrusion 327 allows proximal translation of linear drive 315 by selectively interacting with gear 322, as shown in FIGS. AC, AD, and AE.

Returning to FIGS. 4 and 5, gear 322 is operatively associated with gear 314. In turn, gear 314 is adapted to engage a linear driver 315 and configured to rotate about a central axis "Y." Linear driver 315 is designed to drive a cam sled 428 of tool assembly 116 (see FIG. 6) and may be formed by a rack, a chain or other suitable apparatus. Gear 314 may be replaced by a sprocket or any other suitable apparatus. As discussed above, surgical instrument 100 may be used with any suitable articulating or bendable tool assembly.

Figure 5B:
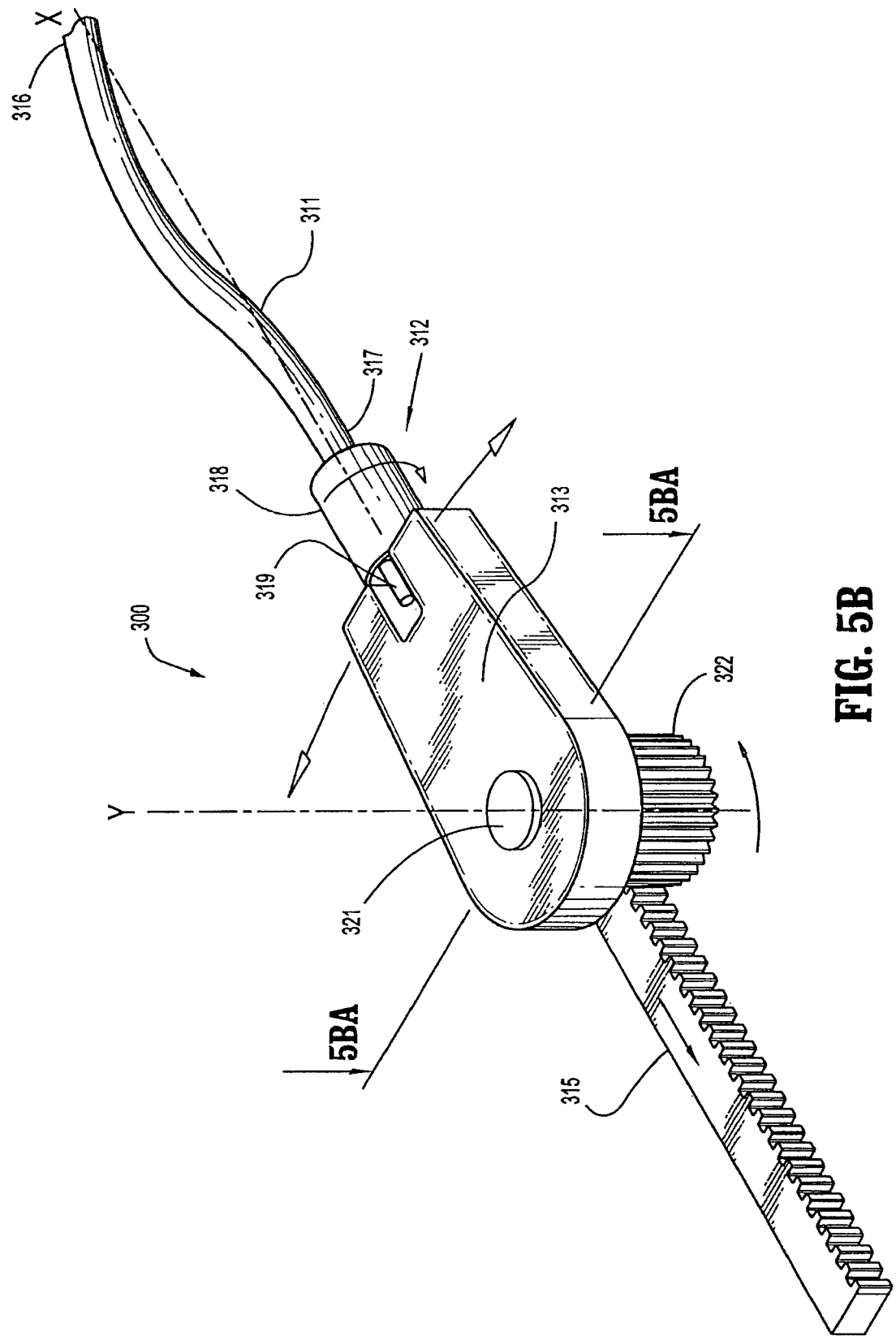
FIG. 5B is a perspective view of a drive mechanism according to an embodiment of the present disclosure.
Figure 5B:
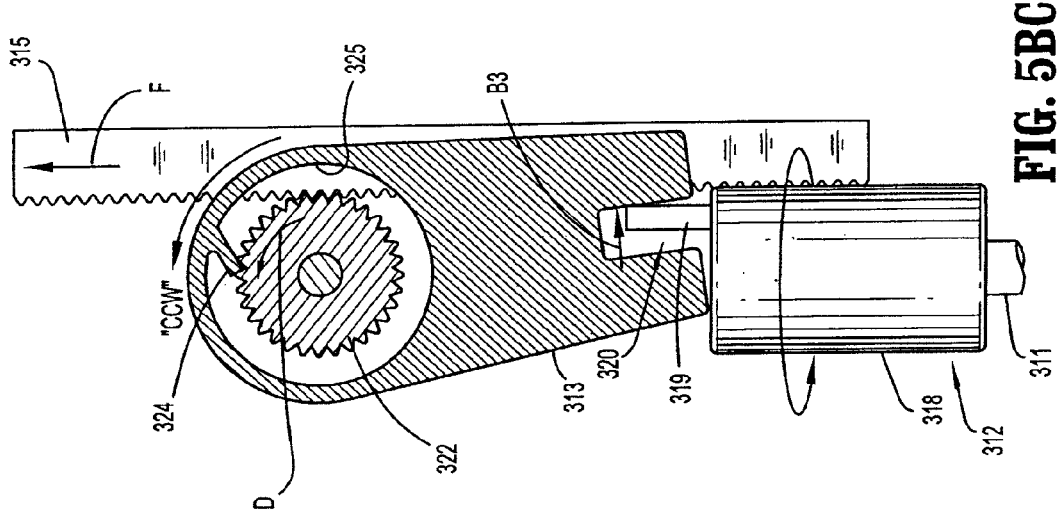
Figure 5B:
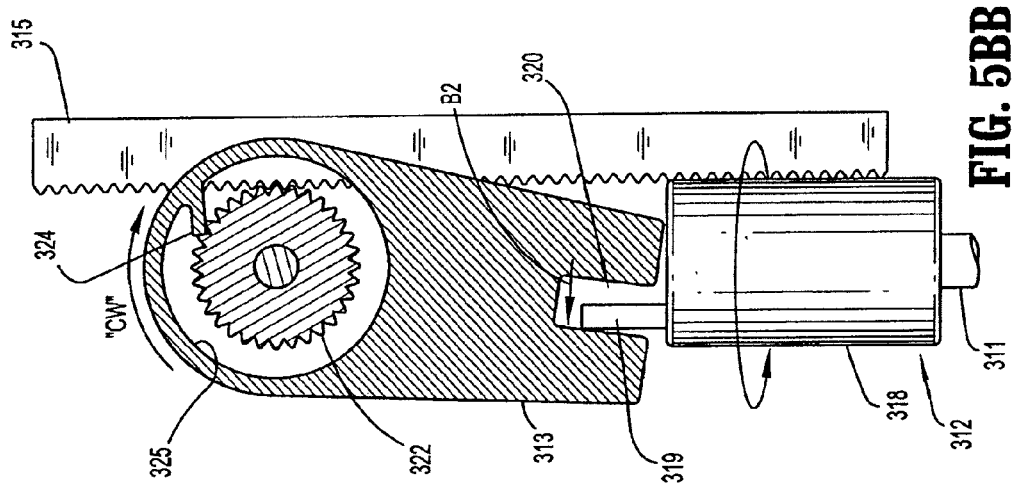
Figure 5B:
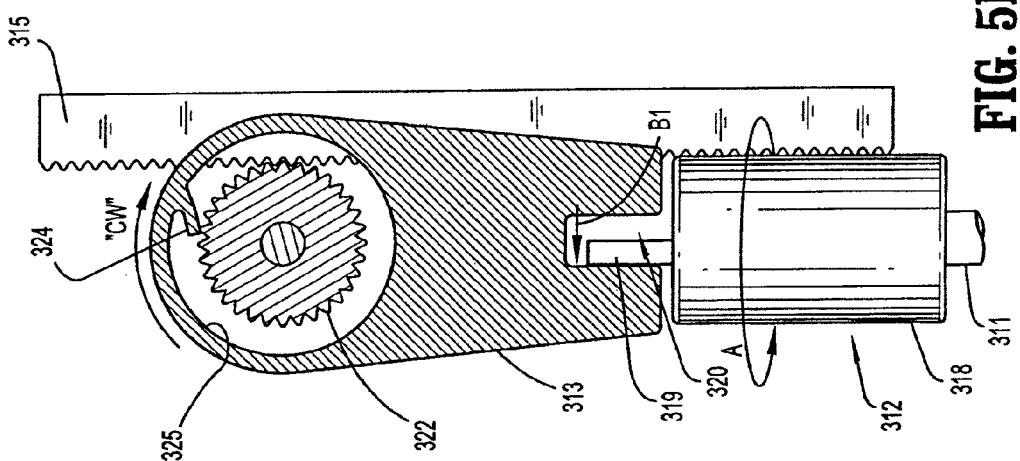

Alternatively, as shown in FIG. 5B, gear 322 can directly engage linear driver 315. In this embodiment, gear 322 extends beyond the boundaries of clutch 313. During operation, the portion of gear 322 clutch 313 that is not covered by clutch 313 engages linear driver 315. As it will be explained in detail below, the rotation of gear 322 causes the distal movement of linear driver 315. This distal movement, in turn, actuates tool assembly 116.

Figure 6:
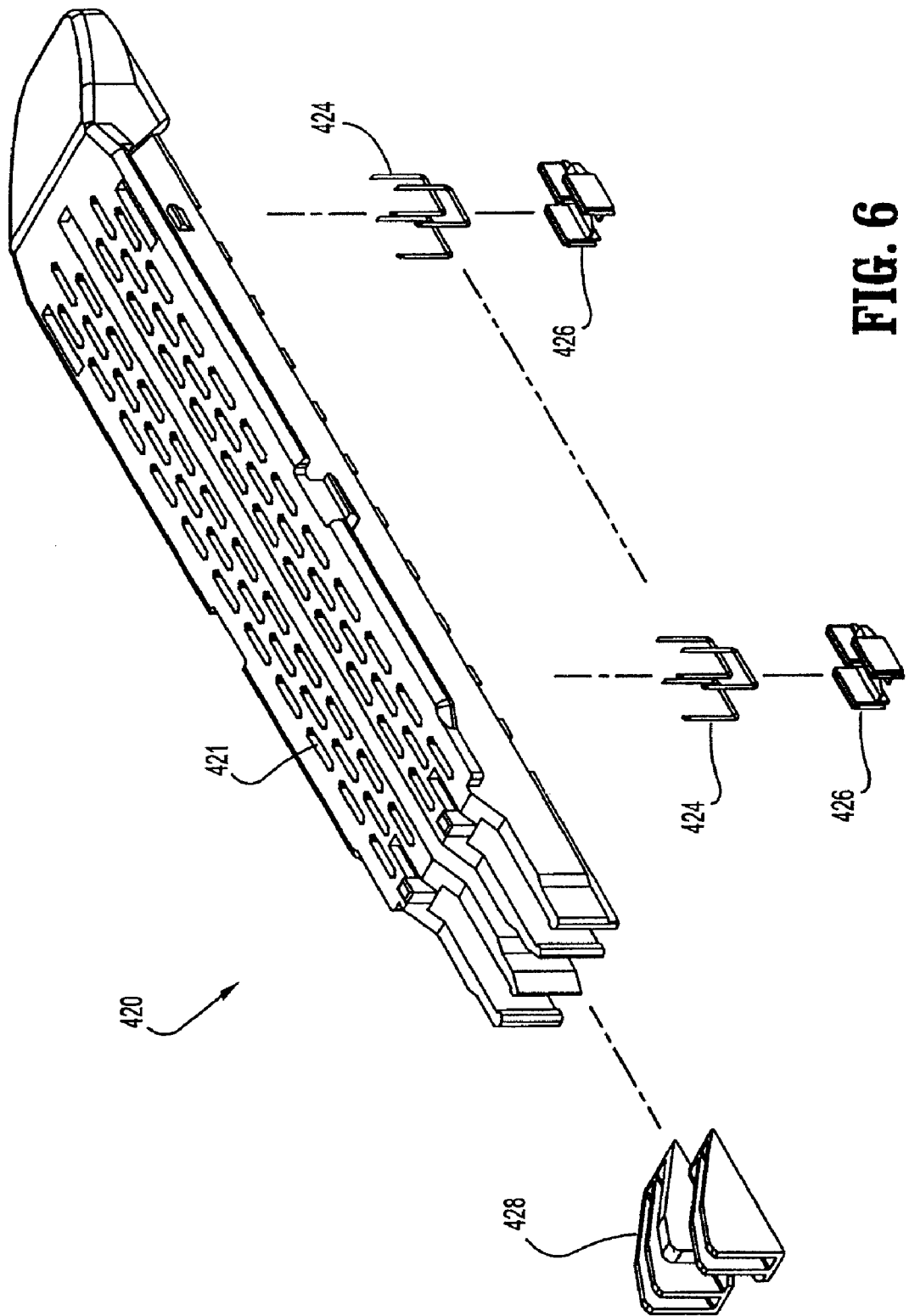
FIG. 6 is an exploded perspective view of a portion of the surgical tool of the surgical instrument of FIG. 1.

As seen in FIG. 6, tool assembly 116 includes, for example, a cartridge assembly 420, as described in U.S. Pat. No. 5,651, 491, the entire contents of which is incorporated herein by reference. Cartridge assembly 420 includes plurality of slots 421 that support a corresponding number of surgical staples 424, a plurality of staple pushers or ejectors 426 adapted and configured to eject the staples from the slots when acted upon by a staple driving force, and an actuation sled 428 which is driven by linear driver 315 to translate through cartridge 420 in a longitudinal direction to transmit a staple driving force to the ejectors.

With reference to FIGS. 7A-7C, in operation, either motor assembly 122 or rotary pneumatic drive assembly 200 rotate drive member 311. The rotation of drive member 311, in turn, produces rotational motion of crank mechanism 312, in the direction shown by arrow "A." The crank mechanism 312 converts the high speed, low torque rotational motion of the drive member 311 to a high torque rocking or oscillating motion of just a few degrees. Since pin 319 is radially offset from the center of distal end surface 322 of rod member 318, the rotation of rod member 318, in the direction shown by arrow "A," initially causes the rocking motion of pin 319 in the direction shown by arrow "B1". As pin 319 begins to move, clutch 313 rotates clockwise, as illustrated by arrow "CW". While rod member 318 continues to rotate, pin 319 continues to move in the direction shown by arrow "B2" and clutch 313 continues to rotate clockwise, as shown by arrow "CW." The continued rotation of rod member 318 eventually causes pin 319 to move in the direction shown by arrow "B3." At this point, the continuing motion of pin 319 causes clutch 313 to rotate counterclockwise, as shown by arrow "CCW."

The rotation of clutch 313 causes the corresponding rotation of gear 322. The rotation of clutch 313 eventually causes the counterclockwise rotation of gear 322, as shown by arrow "D". The rotary motion of first gear 322 causes the rotation of gear 314, as shown by arrow "E." In response to the rotational motion of gear 314, linear driver 315 moves axially with an extremely high force, as illustrated by arrow "F." As linear driver 315 advances, actuator sled 428 translates to operate tool assembly 116. Alternatively, linear driver 315 may be translated directly by gear 322, as illustrated in FIGS. 5BA, 5BB, and 5BC.

In any event, the translation "F" of linear driver 15 produces a force strong enough to operate tool assembly 116 of surgical instrument 100 at angles of at least 90 degrees relative to longitudinal axis "X". The method hereinabove described provides a mechanical advantage of at least 100:1. Mechanism 300, however, can be used for other methods of operation. For instance, mechanism 300 may be utilized to retract actuation sled 428 to its original position after firing surgical instrument 100.

With reference to FIGS. 5AC, 5AD, and 5AE, an operator can retract cam sled 428 by proximally moving linear driver 315 by using embodiment shown in FIG. 5A. To translate linear driver 315 proximally, a user may engage second protrusion 327 and disengage first protrusion 326. Thereafter, motor assembly 122 or rotary pneumatic drive assembly 200 rotates drive member 311. In response thereto, crank mechanism 312 rotates in the direction shown by arrow "A" and converts the high speed, low torque rotational motion of drive member 311 to a high torque rocking or oscillating motion of just a few degrees. In particular, the rotation of rod member 318 initially causes the rocking motion of pin 319 in the direction indicated by arrow "G1." As pin 319 moves, clutch 313 rotates clutch counterclockwise, as illustrated by arrow "CCW." While rod member 318 continues to rotate, pin 319 continues to move in the direction shown by "G2" and clutch 313 continues to rotate counterclockwise, as shown by arrow "CCW." The continued rotation of rod member 318 eventually causes pin 319 to move in the direction shown by arrow "G3." At this point, the continuing motion of pin 319 causes clutch 313 to rotate clockwise, as shown by arrow "CW." The rotation of clutch 313 causes the corresponding rotation of gear 322, as shown by arrow "H." The rotary motion of first gear 322 causes the rotation of gear 314, as shown by arrow "I." In response to the rotational motion of gear 314, linear driver 315 moves proximally, as illustrated in by arrow "J." The proximal translation of linear driver 315 retracts actuator sled 428 to its original position.

The applications of the surgical instrument 100 and the methods of using the same discussed above are not limited to stapling instruments used to attach body tissues, but may include any number of further surgical applications. Modification of the above-described surgical instrument and methods for using the same, and variations of the disclosure that are obvious to those of skill in the art are intended to be within the scope of the claims. For example, other varieties of one way clutches may be employed with surgical instrument 100 or mechanism 300.

What it is claimed:

1. A drive mechanism for a surgical instrument, comprising:
   a drive member;
   a crank operatively coupled to the drive member and including a pin extending distally from a location offset from a center of the crank;

a clutch operatively coupled to the crank and configured to convert a rotary movement of the drive member into movement of the clutch; and a linear driver configured to move longitudinally in response to movement of the clutch.

2. The drive mechanism of claim 1, further comprising a gear rotatably coupled to the clutch, wherein the movement of the clutch causes rotation of the gear.

3. The drive mechanism of claim 2, wherein the gear is configured to engage the linear driver to impart longitudinal motion thereto.

4. The drive mechanism of claim 3, wherein the rotation of the gear causes distal longitudinal motion of the linear driver when the gear and the linear member are engaged with each other.

5. The drive mechanism of claim 1, wherein a longitudinal motion of the linear driver actuates a surgical tool.

6. The drive mechanism of claim 1, wherein the clutch includes a slot dimensioned and configured to receive the pin.

7. The drive mechanism of claim 6, wherein a movement of the pin within the slot converts the rotary movement of the drive member into an oscillating movement of the clutch.

8. A surgical instrument, comprising:

a handle portion;

an elongate portion extending from the handle portion;

an end effector operatively coupled to the elongate portion;

a drive mechanism operatively associated with the handle portion, the drive mechanism including:

a drive member;

a crank operatively coupled to the drive member and including a pin extending distally from a location offset from a center of the crank;

a clutch operatively coupled to the crank, wherein the crank is configured to convert a rotary movement of the drive member into movement of the clutch; and a linear driver configured to move longitudinally in response to the movement of the clutch, wherein the longitudinal motion of the linear driver actuates the end effector.

9. The surgical instrument of claim 8, further comprising a gear rotatably coupled to the clutch, wherein the movement of the clutch causes rotation of the gear.

10. The surgical instrument of claim 9, wherein the gear is configured to engage the linear driver to impart longitudinal motion thereto.

11. The surgical instrument of claim 8, wherein the rotation of the gear causes distal longitudinal motion of the linear driver when the gear and the linear member are engaged with each other.

12. The surgical instrument of claim 8, wherein the clutch includes a slot dimensioned and configured to receive the pin.

13. The surgical instrument of claim 12, wherein a movement of the pin within the slot converts the rotary movement of the drive member into an oscillating movement of the clutch.

14. The surgical instrument of claim 8, wherein the drive member is configured to rotate upon actuation of the handle portion.

* * * * *